(12) United States Patent
Ufer

(10) Patent No.: US 6,843,899 B2
(45) Date of Patent: Jan. 18, 2005

(54) 2D/3D CHEMICAL SENSORS AND METHODS OF FABRICATING AND OPERATING THE SAME

(75) Inventor: Stefan Ufer, Carrboro, NC (US)

(73) Assignee: North Carolina State University, Raleigh, NC (US)

(*) Notice: Subject to any disclaimer, the term of this patent is extended or adjusted under 35 U.S.C. 154(b) by 522 days.

(21) Appl. No.: 10/008,849

(22) Filed: Nov. 6, 2001

(65) Prior Publication Data
US 2003/0085124 A1 May 8, 2003

(51) Int. Cl.[7] .............. G01N 27/30; G01N 27/327; G01N 27/333; H01B 13/00
(52) U.S. Cl. ............. 204/400; 204/403.01; 204/416; 216/2; 216/13; 216/17; 216/41; 216/49; 216/67; 216/75; 216/78
(58) Field of Search ............ 204/400, 403.01–403.14, 204/404, 405, 416–418, 431, 433; 600/345–348; 216/2, 13, 17, 41, 49, 67, 75, 78; 430/313, 316, 317, 319, 320

(56) References Cited

U.S. PATENT DOCUMENTS

| 4,191,950 A | 3/1980 | Levin et al. | |
|---|---|---|---|
| 4,482,882 A | 11/1984 | Luder et al. | |
| 5,670,031 A | 9/1997 | Hintsche et al. | 204/412 |
| 5,951,846 A | 9/1999 | Lewis et al. | |
| 6,110,354 A | * 8/2000 | Saban et al. | 205/775 |

FOREIGN PATENT DOCUMENTS

| DE | 195 09 518 A | 9/1996 | |
|---|---|---|---|
| JP | 07 027731 A | 5/1995 | |
| WO | WO 90/123314 A1 * | 10/1990 | G01N/27/28 |
| WO | WO 94/29708 | 12/1994 | G01N/27/30 |
| WO | WO 97/34140 | 9/1997 | G01N/27/12 |

OTHER PUBLICATIONS

JPO computer translaiton of JP 07–027731 (Masakazu et al.).*

Marzouk et al., *Electrodeposited Iridium Oxide pH Electrode for Measurement of Extracellular Myocardial Acidosis During Acute Ischema*, Analytical Chemistry, vol. 70, No. 23, Dec. 1, 1998, pp. 5054–5061.

Buck et al., *Microfabrication Technology of Flexible Membrane Based Sensors for In Vivo Applications*, Electroanalysis, vol. 7, No. 9, 1995, pp. 846–851.

(List continued on next page.)

*Primary Examiner*—Alex Noguerola
(74) *Attorney, Agent, or Firm*—Myers Bigel Sibley & Sajovec

(57) ABSTRACT

Chemical sensors include a flexible substrate, a flexible lower electrode on the flexible substrate, and a patterned flexible dielectric layer on the flexible lower electrode opposite the flexible substrate. A patterned flexible upper electrode also is included on the patterned flexible dielectric layer opposite the flexible lower electrode. The patterned flexible dielectric layer and the patterned flexible upper electrode are patterned to establish a first current flow path between the flexible lower electrode and the patterned flexible upper electrode through the chemical, if present, upon application of voltage between the flexible lower electrode and the patterned flexible upper electrode. The flexible lower electrode also may be patterned to establish a second current flow path between portions of the patterned flexible lower electrode through the chemical, if present, upon application of voltage between the portions of the patterned flexible lower electrodes. The flexible upper electrode also may be patterned to establish a third current flow path between portions of the patterned flexible upper electrode through the chemical, if present, upon application of voltage between the portions of the patterned flexible upper electrode. A rigid substrate also may be used.

46 Claims, 8 Drawing Sheets

OTHER PUBLICATIONS

Cosofret et al., *Microfabricated Sensor Arrays Sensitive to pH and $K^+$ for Ionic Distribution Measurements in the Beating Heart*, Analytical Chemistry, vol. 67, No. 10, May 15, 1995, pp. 1647–1653.

Horiuchi et al., *Limiting Current Enhancement by Self–Induced Redox Cycling on a Micro–Macro Twin Electrode*, J. Electrochem. Soc., vol. 138, No. 12, Dec. 1991, pp. 3549–3553.

Niwa et al., *Fabrication and Characteristics of Vertically Separated Interdigitated Array Electrodes*, J. Electroanal. Chem., vol. 267, 1989, pp. 291–297.

Aoki, *Theory of the Steady–Stated Current of a Redox Couple at Interdigitated Array Electrodes of Which Pairs Are Insulated Electrically by Steps*, J. Electroanal. Chem., vol. 270, 1989, pp. 35–41.

Aoki et al., *Quantitative Analysis of Reversible Diffusion–Controlled Currents of Redox Soluble Species at Interdigitated Array Electrodes Under Steady–State Conditions*, J. Electroanal. Chem, vol. 256, 1988, pp. 269–282.

International Search Report, PCT/US02/34485, Jul. 18, 2003.

* cited by examiner

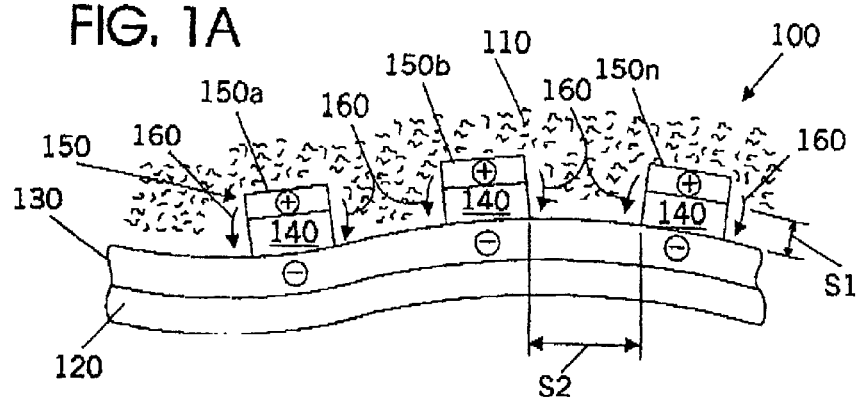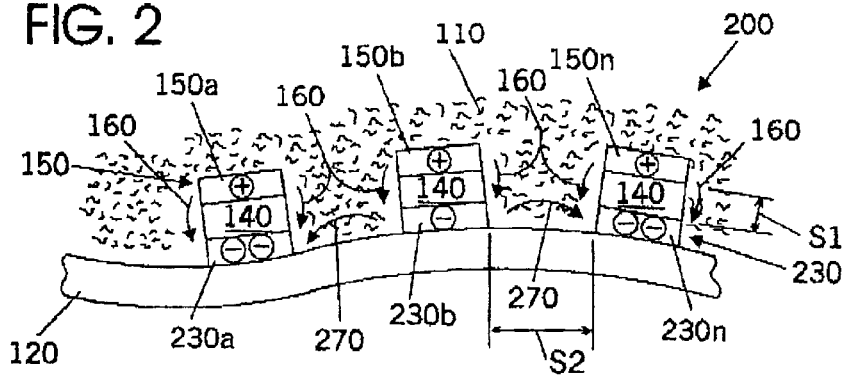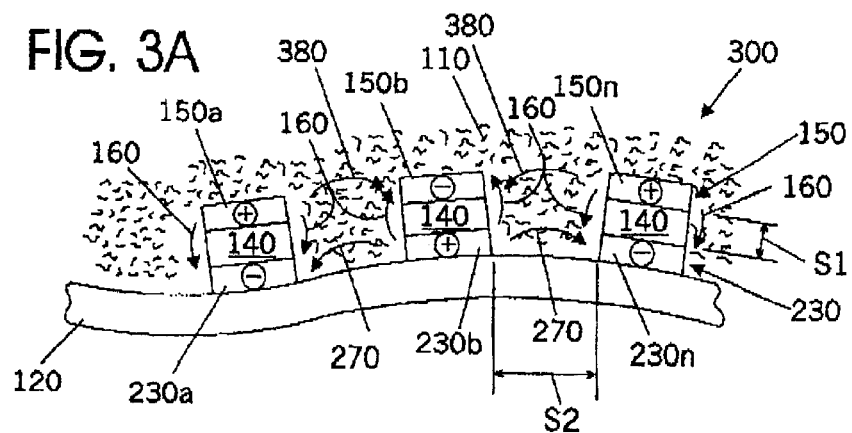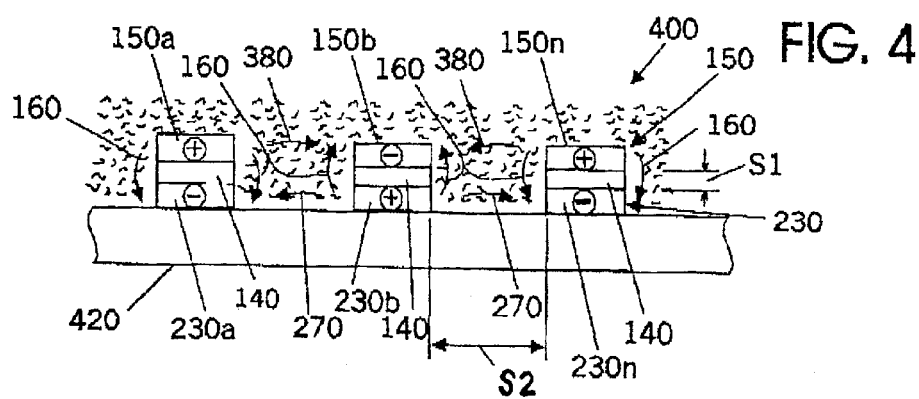

2D/3D CHEMICAL SENSORS AND METHODS OF FABRICATING AND OPERATING THE SAME

FIELD OF THE INVENTION

This invention relates to sensors and methods of fabricating and operating the same, and more particularly to chemical sensors and methods of fabricating and operating the same.

BACKGROUND OF THE INVENTION

Chemical sensors are widely used to sense one or more chemicals. The chemicals can be a solid, liquid and/or gas and/or one or more constituents and/or combinations thereof. The constituent can include an inorganic molecule, an organic molecule, compounds thereof and/or combinations thereof, and may be detected using one or more activators, such as an enzyme. Chemical sensors are widely used, for example in chemical analytics and/or as process controls in various fields, such as biotechnology, environmental protection and/or health care. For example, chemical sensors used in medical diagnostic or evaluation procedures often use electrochemical detection of an analyte provided by dry or fluid/liquid chemistries/electrolytes.

As is well known to those having skill in the art, a chemical sensor may employ one or more interdigitated electrodes that include a plurality of spaced apart interdigitated fingers. See, for example, U.S. Pat. No. 5,670,731 to Hintsche et al. entitled Electrochemical Sensor, and published PCT Application WO 97/34140 to Hintsche, entitled Detection of Molecules and Molecule Complexes. In sensors that use interdigitated electrodes, it may be desirable to have a small spacing between the fingers thereof, so as to allow small diffusion lengths for electrochemically active species, and thereby allow increased sensitivity of the sensor to small concentrations and/or small changes in concentration.

Unfortunately, in order to provide the small spacings between fingers of interdigitated electrodes, microelectronic processing methods may need to be used. See, for example, Niwa et al., *Fabrication and Characteristics of Vertically Separated Interdigitated Array Electrodes*, J. Electroanal. Chem., Vol. 267, 1989, pp. 291–297; Aoki, *Theory of the Steady-State Current of a Redox Couple at Interdigitated Array Electrodes of Which Pairs are Insulated Electrically by Steps*, J. Electroanal. Chem., Vol. 270, 1989, pp. 35–41; Aoki, *Quantitative Analysis of Reversible Diffusion-Controlled Currents of Redox Soluble Species at Interdigitated Array Electrodes Under Steady-State Conditions*, J. Electroanal. Chem., Vol. 256 1988, pp. 269–282; and Horiuchi et al., *Limiting Current Enhancement by Self-Induced Redox Cycling on a Micro-Macro Twin Electrode*, J. Electrochem. Soc., Vol. 138, No. 12, December 1991, pp. 3549–3553. These microelectronic processing methods may employ relatively high cost microelectronic substrates, such as silicon wafers, and/or relatively complex and/or expensive fabrication processes, such as high resolution lithography, to achieve the desired spacing. The chemical sensors that are produced thereby may be too expensive for some intended uses. For example, it may be desirable to provide a low cost, single-use disposable sensor that can be used as a drug abuse monitor for sensing small concentrations of drugs in urine and/or other biological samples.

SUMMARY OF THE INVENTION

Chemical sensors according to embodiments of the invention include a flexible substrate, a flexible lower electrode on the flexible substrate, and a patterned flexible dielectric layer on the flexible lower electrode opposite the flexible substrate. A patterned flexible upper electrode also is included on the patterned flexible dielectric layer opposite the flexible lower electrode. The patterned flexible dielectric layer and the patterned flexible upper electrode are patterned to establish a current flow path between the flexible lower electrode and the patterned flexible upper electrode through the chemical, if present, upon application of voltage between the flexible lower electrode and the patterned flexible upper electrode. For example, the patterned flexible upper electrode can include a plurality of spaced apart fingers that are spaced apart from one another by at least an order of magnitude more than the thickness of the patterned flexible dielectric layer. A flexible insulation layer also may be included on the flexible lower electrode, flexible dielectric layer and/or flexible upper electrode, which can include openings for bond pads and/or sensing areas while covering traces between bond pads and electrodes.

In these embodiments of the invention, relatively small spacing may be provided between the flexible lower electrode and the patterned flexible upper electrode, which can be defined by the thickness of the patterned flexible dielectric layer, rather than by lithography. Moreover, these embodiments of the invention can provide chemical sensors that use a flexible substrate, flexible electrodes and/or flexible dielectric layers, which can be lower cost than conventional microelectronic substrates such as silicon wafers. Moreover, flexible substrates may accommodate tissue movements surrounding the area of implantation of an in vivo sensor. Accordingly, low cost and/or high sensitivity chemical sensors may be provided that may be used, for example, in in vivo applications.

Embodiments of chemical sensors that were described above may provide a current flow path that is not parallel to the substrate face, and preferably is orthogonal to the substrate face, which may be referred to as a vertical current flow path. In other embodiments, the flexible lower electrode is a patterned flexible lower electrode that can establish a second current flow path between portions of the patterned flexible lower electrode through the chemical, if present, upon application of voltage between the portions of the patterned flexible lower electrodes. In yet other embodiments, the flexible upper electrode is patterned to establish a third current flow path between portions of the patterned flexible upper electrode through the chemical, if present, upon application of voltage between the portions of the patterned flexible upper electrode. The second and third current flow paths may extend in a direction that is generally parallel to the substrate face, referred to as a horizontal current flow path. Accordingly, these embodiments of the invention may provide current flow paths in two different directions, such as vertical and horizontal current flow paths. These embodiments of chemical sensors, therefore, may provide three-dimensional current flow in contrast with conventional two-dimensional (either horizontal or vertical) current flow paths, in conventional interdigitated array electrodes.

In yet other embodiments of the present invention, the patterned flexible upper electrode and the patterned flexible lower electrode both include a plurality of spaced apart fingers. The patterned flexible dielectric layer, the patterned flexible lower electrode and the patterned flexible upper electrode are patterned to establish a first current flow path between the patterned flexible lower electrode and the patterned flexible upper electrode through the chemical, if present, a second current flow path between adjacent fingers of the patterned flexible lower electrode through the chemical, if present, and a third current flow path between the adjacent fingers of the patterned flexible upper electrode through the chemical, if present, upon application of voltage between the adjacent fingers of the patterned flexible lower electrode, between the adjacent fingers of the patterned flexible upper electrode and between adjacent fingers of the patterned upper and lower flexible electrodes. Accordingly, three-dimensional current flow paths may be provided that include both horizontal and vertical current flow paths. The three-dimensional current flow paths can provide higher sensitivity than a similarly sized chemical sensor that only employs a two-dimensional (horizontal or vertical) current flow path.

Embodiments of the invention that employ three-dimensional current flow paths having both a horizontal component and a vertical component also may be used with chemical sensors that use a rigid substrate, dielectric and/or electrodes, rather than a flexible substrate, dielectric and/or electrodes. Accordingly, embodiments of the invention that include three-dimensional current flow paths can include a substrate, a lower electrode on the substrate, a patterned dielectric layer on the lower electrode opposite the substrate and a patterned upper electrode on the patterned dielectric layer opposite the lower electrode. The patterned dielectric layer and the patterned upper electrode are patterned to establish a first current flow path between the lower electrode and the patterned upper electrode through the chemical, if present, upon application of voltage between the lower electrode and the patterned upper electrode, and to establish a second current flow path between portions of the patterned upper electrode through the chemical, if present, upon application of voltage between the portions of the patterned upper electrode.

In yet other embodiments, the lower electrode is a patterned lower electrode that is patterned to establish a third current flow path between portions of the patterned lower electrode through the chemical, if present, upon application of voltage between the portions of the lower electrode. In still other embodiments, the patterned upper electrode and/or the patterned lower electrode include a plurality of spaced apart fingers which are patterned to establish the first, second and third current flow paths.

Chemical sensors may be fabricated, according to method embodiments of the invention, by forming a flexible lower electrode on a flexible substrate, forming a flexible dielectric layer on the flexible lower electrode opposite the flexible substrate, and forming a patterned flexible upper electrode on the flexible dielectric layer opposite the flexible lower electrode. The flexible dielectric layer is patterned using the patterned flexible upper electrode as a mask, to establish a current flow path between the flexible lower electrode and the patterned flexible upper electrode through the chemical, if present, upon application of voltage between the flexible lower electrode and the patterned flexible upper electrode.

In other method embodiments, the flexible lower electrode is a patterned flexible lower electrode. Patterned flexible lower electrodes and/or patterned flexible upper electrodes may be fabricated by laminating a flexible photoresist layer onto an electrode layer, and selectively exposing and developing the flexible photoresist layer. The electrode is then patterned using the flexible photoresist layer that has been exposed and developed. The flexible photoresist layer that has been exposed and developed then is removed from the patterned layer. Moreover, in other embodiments, the flexible dielectric layer is patterned by reactive ion etching the flexible dielectric layer using the patterned flexible upper electrode as a mask.

When using a flexible substrate, a plurality of chemical sensors also may be fabricated using continuous processing techniques, according to embodiments of the invention. In these embodiments, a series of laterally spaced apart flexible lower electrodes is formed on the flexible substrate, such as a continuous roll flexible substrate. A flexible dielectric layer is formed on the series of laterally spaced apart flexible lower electrodes opposite the flexible substrate. A series of patterned flexible upper electrodes is formed on the dielectric layer, a respective one of which is opposite a respective one of the series of flexible lower electrodes. The flexible dielectric layer is patterned using the series of patterned flexible upper electrodes as a mask, to establish a current flow path between a respective flexible lower electrode and a respective patterned flexible upper electrode through the chemical, if present, upon application of voltage between a flexible lower electrode and the patterned flexible upper electrode. In other method embodiments, a series of laterally spaced apart patterned flexible lower electrodes may be fabricated.

Finally, according to still other method embodiments of the invention, chemical sensors that include three-dimensional current flow paths may be used to allow increased sensitivity over conventional two-dimensional current flow path chemical sensors. Thus, chemical sensors that include a substrate, a patterned lower electrode on the substrate, a patterned dielectric layer on the lower electrode and a patterned upper electrode on the patterned dielectric layer may be used to sense a chemical. In some embodiments, a chemical is sensed by applying voltage between adjacent portions of the patterned upper electrode, between adjacent portions of the patterned lower electrode and between adjacent portions of the patterned upper and lower electrodes. In other embodiments, the patterned upper electrode and the patterned lower electrode both include a plurality of spaced apart fingers. In these embodiments, voltage is applied between adjacent spaced apart fingers of the patterned upper electrode, between adjacent spaced apart fingers of the patterned lower electrode and between adjacent fingers of the patterned upper and lower electrodes. Accordingly, low cost and/or high sensitivity chemical sensing may be provided.

BRIEF DESCRIPTION OF THE DRAWINGS

FIGS. 1A, 2, 3A and 4 are side cross-sectional views of chemical sensors according to embodiments of the present invention.

DETAILED DESCRIPTION OF THE PREFERRED EMBODIMENT

Figure 1B:
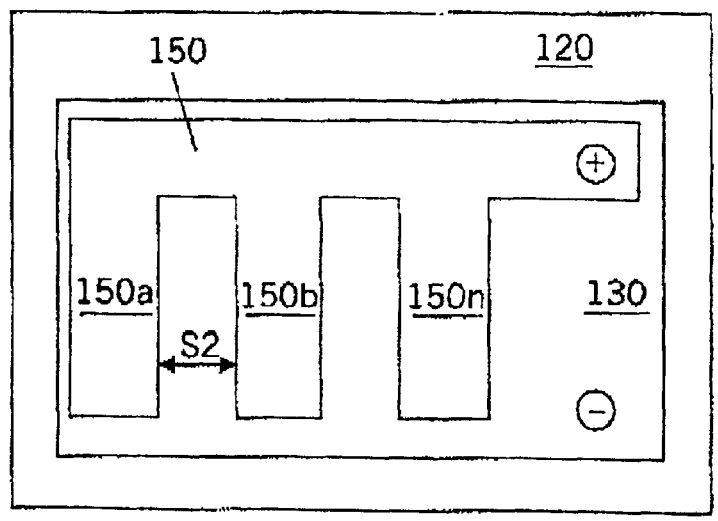
FIGS. 1B, 3B and 8 are top plan views of chemical sensors according to embodiments of the invention.

The present invention now will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the thickness of layers, regions, components or features are exaggerated for clarity. Like numbers refer to like elements throughout. It will be understood that when an element such as a layer, region or substrate is referred to as being "on" another element, it can be directly on the other element or intervening elements may also be present. In contrast, when an element is referred to as being "directly on" another element, there are no intervening elements present.

FIGS. 1A and 1B are a side cross-sectional view and a top view, respectively, of chemical sensors according to embodiments of the present invention. As shown in FIGS. 1A and 1B, these embodiments of chemical sensors 100 sense a chemical 110 which can include a solid, liquid, and/or gas and/or one or more constituents and/or combinations thereof. The constituents can be an inorganic molecule, an organic molecule, compounds thereof and/or combinations thereof, and may be detected using one or more activators such as an enzyme and/or electrochemical mediators.

Still referring to FIGS. 1A and 1B, the chemical sensor 100 includes a flexible substrate 120. The flexible substrate 120 preferably is an elastomer such as plastic, including polyimide films (Kapton®, Upilex® and the like). Although the flexible substrate 120 is shown as comprising a single material, it will be understood that multiple layers of materials may be used, and that conductive portions, such as vias, also may be included therein, to provide external electrical connection paths.

Still referring to FIGS. 1A and 1B, a flexible lower electrode 130 is included on the flexible substrate 120. The flexible lower electrode may comprise one or more conductive materials, such as gold, that is sufficiently thin, for example less than about 50 $\mu$m thick, so as to be flexible. Other conductive materials, such as platinum, palladium, copper and/or non-metallic conductors also may be used. In FIGS. 1A and 1B, the flexible lower electrode 130 is an unpatterned layer. However, as will be described below, in other embodiments, patterned flexible lower electrodes may be used.

Still referring to FIGS. 1A and 1B, a patterned flexible dielectric layer 140 is provided on the flexible lower electrode 130 opposite the flexible substrate 120. The patterned flexible dielectric layer 140 may comprise one or more flexible dielectric materials, including organic dielectric materials such as polyimide, that are inherently flexible and/or are sufficiently thin, such as less than about 1 $\mu$m, to remain flexible. Other materials that may be used for the patterned flexible dielectric layer 140 include the materials described above for the flexible substrate 120, materials formed by Plasma Enhanced Chemical Vapor Deposition (PECVD), such as silicon dioxide and/or silicon nitride, and/or Diamond-Like Carbon (DLC) coatings. DLC coatings are described, for example, in application Ser. No. 09/826,431, entitled Adsorbing and Non-Adsorbing Surfaces for Biological Materials, filed Apr. 4, 2001, the disclosure of which is hereby incorporated herein by reference in its entirety as if set forth fully herein.

Finally, still referring to FIGS. 1A and 1B, a patterned flexible upper electrode 150 is provided on the patterned flexible dielectric layer 140 opposite the flexible lower electrode 130. In some embodiments, the patterned flexible upper electrode 150 includes a plurality of spaced apart portions, such as fingers 150a–150n that are spaced apart from one another. It will be understood that any number of fingers 150a–150n may be used. The patterned flexible upper electrode 150 may comprise the same materials as the flexible lower electrode 130, but need not comprise the same material. It also will be understood that, although the flexible substrate 120, the flexible lower electrode 130, the patterned flexible dielectric layer 140 and the patterned flexible upper electrode 150 are illustrated in the figures as having uniform thickness and equal spacings, nonuniform thicknesses and/or spacings may be provided. A flexible insulation layer also may be included on the flexible lower electrode 130, flexible dielectric layer 140 and/or flexible upper electrode 150, which can include openings for bond pads and/or sensing areas while covering traces between bond pads and electrodes.

As shown by the arrows in FIG. 1A, the patterned flexible dielectric layer 150 and the patterned flexible upper electrode 140 are patterned to establish a current flow path 160 between the flexible lower electrode 130 and the patterned flexible upper electrode 150 through the chemical 110, if present, upon application of voltage between the flexible lower electrode 130 and the patterned flexible upper electrode 150. As also shown in FIG. 1, the current flow path 160 extends at least partially along a direction that is nonparallel to the substrate. More specifically, the current flow path 160 extends partially along a direction that is orthogonal to the substrate face. In the embodiments shown, this current flow path 160 may be referred to as a vertical current flow path.

Embodiments of the invention as illustrated in FIGS. 1A and 1B may be fabricated on flexible substrates 120 which can be lower cost than conventional microelectronic substrates, such as silicon wafers. Moreover, low cost continuous fabrication processing may be used, for example using rolls of flexible substrate material, as will be described in detail below. Relatively small spacing may be provided between the flexible lower electrode 130 and the patterned flexible upper electrode 150, that may be determined by the thickness S1 of the patterned flexible dielectric layer 140, rather than by the distance S2 between fingers 150a–150n in the patterned flexible upper electrode 150.

Thus, in some embodiments, the spaced apart fingers 150a–150n are spaced apart from one another by a distance S2 that is at least an order of magnitude more than the thickness S1 of the patterned flexible dielectric layer 140. In some embodiments, the patterned flexible dielectric layer 140 is between about 0.25 $\mu$m and about 2 $\mu$m thick, and adjacent fingers such as 150a and 150b in the patterned flexible upper electrode 150 are spaced apart from one another by between about 5 $\mu$m and about 50 $\mu$m. Thus, high resolution photolithography need not be used to obtain a desired sensitivity.

Finally, in FIGS. 1A and 1B, the voltage differential that is applied between the flexible lower electrode 130 and the patterned flexible upper electrode 150 is indicated by ⊕ and a ⊖ on the patterned flexible upper electrode 150 and on the flexible lower electrode 130, respectively. It will be understood, however, that, in all figures herein, these polarities may be reversed. Moreover, positive and negative symbols are used to indicate relative voltage differentials, rather than absolute voltages so that, for example, one of the voltages may be ground voltage. The voltage that is applied to the flexible lower electrode 130 need not be uniform. Moreover, the voltages applied to the fingers 150a–150n of the patterned flexible upper electrode 150 also need not be uniform. Finally, alternating current (AC) and/or direct current (DC) voltages may be applied, and scanning of voltages across fingers 150a–150n may be used. The voltages may be applied using internal and/or external contacts using techniques that are well known to those having skill in the art.

Thus, embodiments of the present invention as illustrated, for example, in FIGS. 1A and 1B, can provide InterDigitated Array (IDA) electrodes that are closely spaced so that small diffusion lengths for electrochemically-active molecules may be provided. Smaller species which are reduced on one electrode can diffuse fast enough to an adjacent electrode to be oxidized again. This recycling process of electrochemically active molecules can provide amplification of current signals. These amplification effects by electrochemical recycling of reversible redox molecules may be apparent with sensors of structural separations of between about 0.75 μm and about 10 μm. Lateral dimensions may be difficult to control precisely with microelectronic fabrication techniques compared with controlling vertical dimensions, such as film thicknesses. For example, dielectric films can be deposited accurately down to about 10 nm or less. The thickness of a dielectric film can be selected so that it controls the electrode separation in embodiments of FIGS. 1A and 1B, rather than its lateral geometry as in conventional horizontal interdigitated array electrodes. Chemical sensors according to embodiments of the invention may be fabricated at millimeter, micrometer and/or nanometer scales.

It also will be understood that the fabrication of interdigitated electrodes on flexible substrates 120 may use material properties of the flexible substrate 120, the flexible lower electrode 130, the patterned flexible dielectric layer 140 and/or the patterned flexible upper electrode 150. For example, dielectric materials that generally are used for thin film processing on silicon substrates may not be compatible with the flexible substrate 120.

Figure 8:
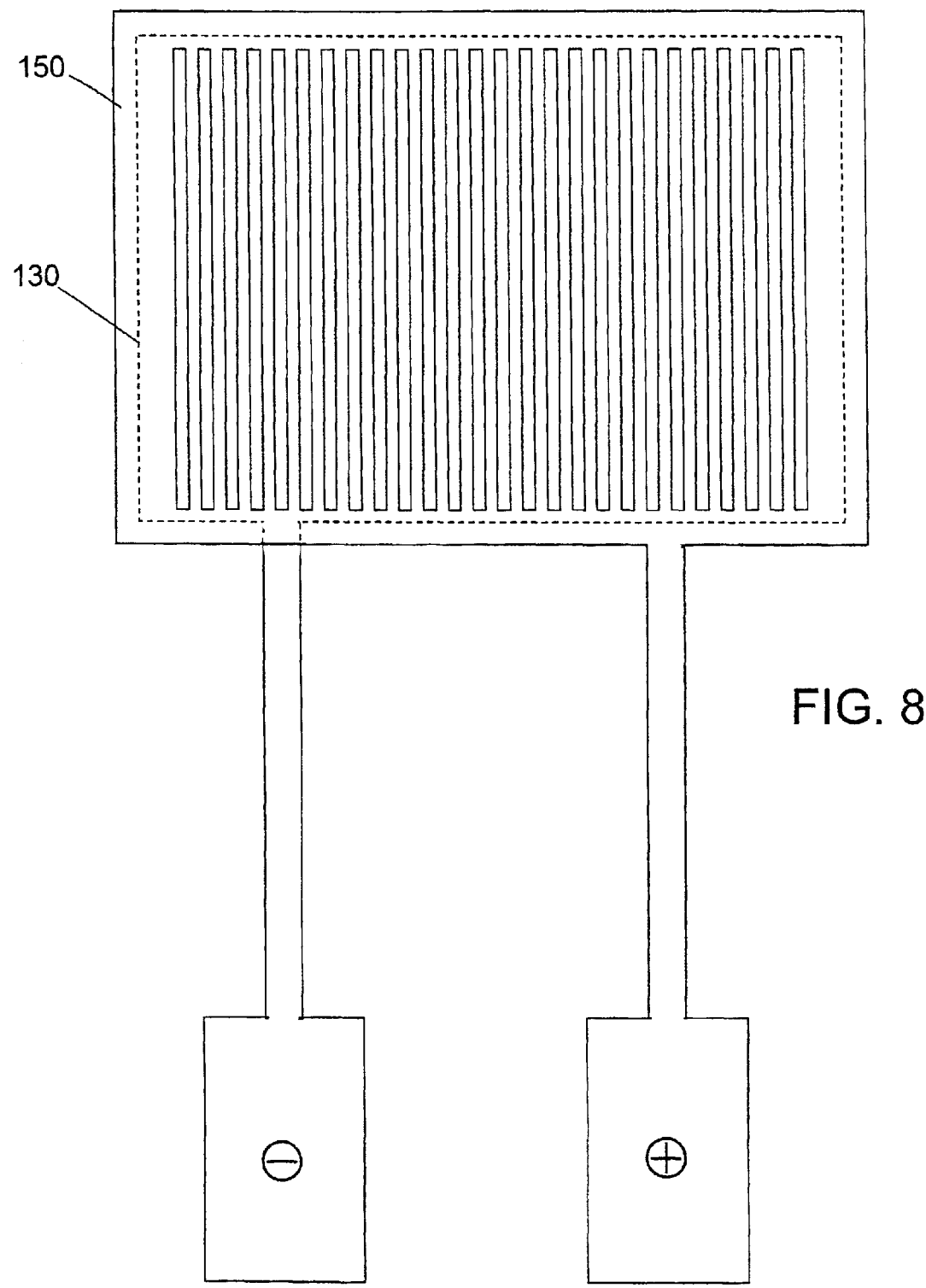

FIG. 8 is a top view of other chemical sensors according to embodiments of the present invention. FIG. 8 is similar to FIG. 1B, except that a large number of fingers in the upper electrode 150 is shown and separate bond pads ⊖, ⊕ for the lower electrode 130 and upper electrode 150, respectively, are shown. Similar to FIG. 1B, a rectangular lower electrode 130 is included.

FIG. 2 illustrates other chemical sensors according to embodiments of the present invention. These embodiments of chemical sensors 200 may include a flexible substrate 120, a patterned flexible dielectric layer 140, and a patterned flexible upper electrode 150, as were described above in connection with FIGS. 1A and 1B. However, embodiments of FIG. 2 also include a patterned flexible lower electrode 230 that may comprise the same materials as the flexible lower electrode 130 of FIGS. 1A and 1B, but that is patterned, for example, to provide a plurality of spaced apart fingers 230a–230n.

The patterned flexible lower electrode 230 can establish a second current flow path 270 between portions, such as fingers 230a–230n, of the patterned flexible lower electrode 230 through the chemical 110, if present, upon application of voltage between the portions of the patterned flexible lower electrode 230, such as the fingers 230a–230n. The second current flow path 270 can extend generally along the substrate face and, therefore, may be regarded as a horizontal current flow path.

As shown in FIG. 2, voltage differentials may be applied between the portions, such as the fingers 230a–230n, of the patterned flexible lower electrode, by providing various levels of negative voltage, shown by ⊖ and ⊖⊖, in FIG. 2. It will be understood, however, that various combinations of voltage differentials may be provided that can establish the first (vertical) current flow path 160 and the second (horizontal) current flow path 270. Thus, three-dimensional current flow in chemical sensors may be provided.

Accordingly, chemical sensors according to embodiments of FIG. 2, can allow current flow in three dimensions, in contrast with conventional chemical sensors that may allow current flow either in the horizontal direction or in the vertical direction. Three-dimensional current flow can provide further amplification of low current signals, and can increase the sensitivity of the chemical sensors, compared to a similarly sized chemical sensor that only employs a two-dimensional current flow path.

It also will be understood that other embodiments can provide a second current flow path 270 by providing voltage differentials between the spaced apart portions, such as fingers 150a–150n, of the upper electrode 150 of FIG. 1, while allowing the lower electrode 130 to remain unpatterned. Thus, the horizontal current flow path may extend among portions of the upper electrode and/or among portions of the lower electrode.

Figure 3B:
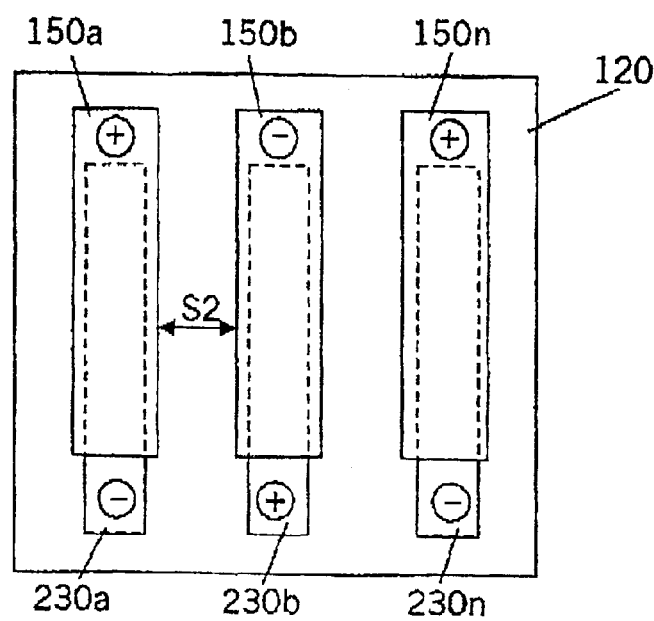

FIGS. 3A and 3B are a side cross-sectional view and a top view, respectively, of other embodiments of chemical sensors 300 of the present invention, wherein differential voltage also is applied between portions, such as fingers 150a–150n, of the patterned flexible upper electrode 150, to establish a third current flow path 380 between the portions of the patterned flexible upper electrode 150, such as between the adjacent spaced apart fingers 150a–150n thereof. Accordingly, even further increases in sensitivity may be obtained by providing two concurrent horizontal current flow paths 270 and 380. It will be understood that FIGS. 3A and 3B illustrate establishing the first, second and third current flow paths 160, 270 and 380 by applying alternating positive and negative voltages, as shown. However, as was the case with embodiments of FIGS. 1A, 1B and 2, many other voltage differential patterns may be used to establish the current flow paths shown in FIGS. 3A and 3B.

Moreover, it will be understood that in embodiments of FIGS. 2 and 3A–3B, it may be desirable to provide reduced spacing between the portions, such as the spaced apart fingers 230a–230n of the patterned flexible lower electrode 230 and/or the spaced apart fingers 150a–150n patterned flexible upper electrode 150, so as to increase the amount of current flow in the second and third current flow paths 270 and 380. Thus, spacings S2 of about 1 μm and finger widths of about 1 μm may be provided. Finally, it also will be understood that internal and/or external power supply contacts may be provided, so as to provide the desired voltage differentials of FIGS. 2 and 3A–3B using techniques well known to those having skill in the art.

As was described above in connection with FIGS. 2 and 3A–3B, increased sensitivity may be provided by three-dimensional current paths, according to embodiments of the invention, compared to conventional two-dimensional current paths. Three-dimensional current paths according to embodiments of the invention may be used with conventional silicon or other rigid substrates, to allow improved sensitivity to be provided in these sensors, as well. Thus, for example, FIG. 4 is a cross-sectional view of chemical sensors 400 according to embodiments of the present invention, wherein a rigid substrate 420, such as a conventional silicon substrate, is provided. Flexible or rigid patterned lower electrodes 230, dielectric layers 140 and/or upper electrodes 150 may be used. Voltage differentials of FIG. 2 and/or FIGS. 3A–3B may be applied to provide three-dimensional current flow paths. Accordingly, the sensitivity of conventional current sensors also may be improved.

Accordingly, as was described above in connection with FIGS. 1–4, a pattern of the upper 150 and/or lower 130/230 electrodes can provide means for establishing a first current flow path 160 between the lower electrode and the upper electrode through the chemical, if present, upon application of between the lower electrode and the upper electrode, and for establishing a second current flow path 380 between portions of the patterned upper electrode through the chemical, if present, upon application of voltage between the portions of the upper electrode. The pattern also can provide means for establishing a third current flow path 270 between portions of the lower electrode through the chemical, if present, upon application of voltage between the portions of the lower electrode. As was described in detail above, many different configurations of patterned upper and/or lower electrodes and patterned dielectric layers may embody means for establishing these current flows according to embodiments of the present invention. Moreover, other patterns of lower, upper and/or other electrodes may be used.

FIGS. 5A–5H are side cross-sectional views of chemical sensors according to embodiments of the present invention during intermediate fabrication steps according to embodiments of the present invention. These embodiments may be used to fabricate embodiments of chemical sensors of FIGS. 1A and 1B. Similar method embodiments may be used to fabricate chemical sensors of FIGS. 2–4.

Figure 5A:
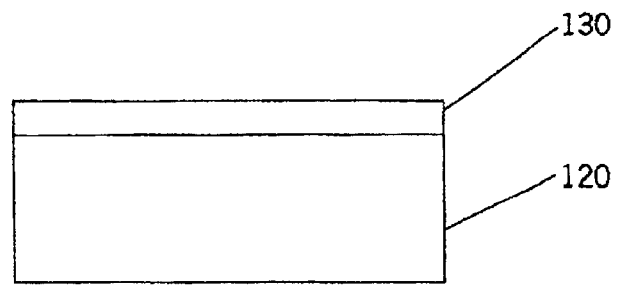
FIGS. 5A–5I and 6A–6I are side cross-sectional views of chemical sensors according to embodiments of the present invention during intermediate fabrication steps according to embodiments of the present invention.
Figure 5B:
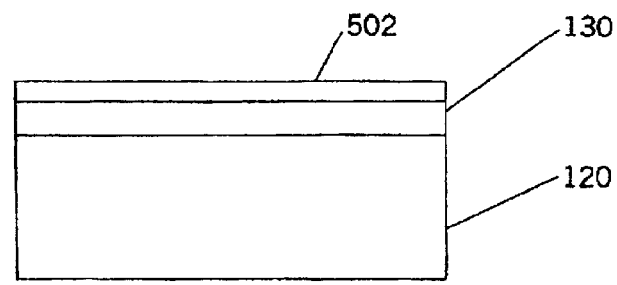
Figure 5C:
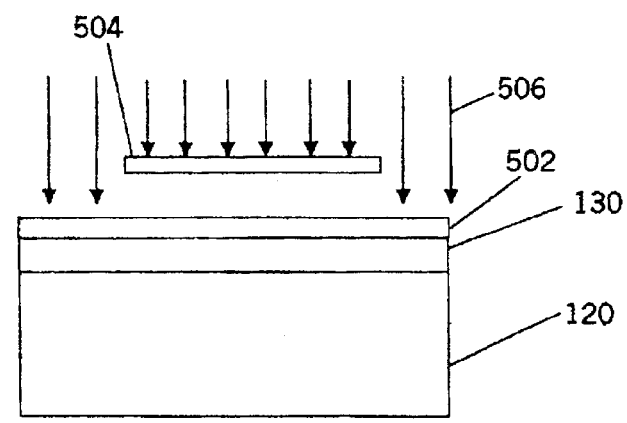
Figure 5D:
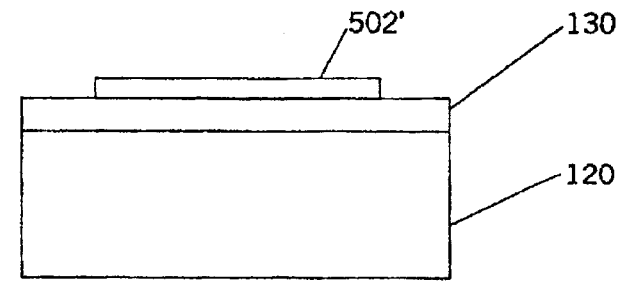
Figure 5E:
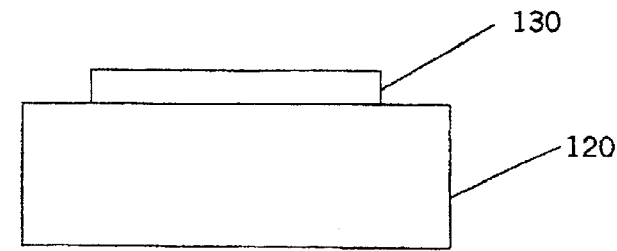

Referring now to FIG. 5A, a flexible lower electrode 130 is formed on a flexible substrate 120. For example, a layer of gold may be deposited on a flexible Kapton® substrate. Referring to FIG. 5B, a layer of photoresist 502 may be laminated, coated and/or otherwise formed on the flexible lower electrode 130. Referring to FIG. 5C, a mask 504 may be used to selectively expose the photoresist 502 to incident radiation 506, to thereby form patterned photoresist 502' (FIG. 5D). As shown in FIG. 5E, the patterned photoresist 502' may be used as a mask to define the flexible lower electrode 130, for example to define a plurality of lower electrodes 130 for a plurality of sensors on a common substrate. The photoresist 502' then may be removed. It will be understood that other conventional patterning techniques may be used, such as lift-off, shadow masking and/or laser ablation.

Figure 5F:
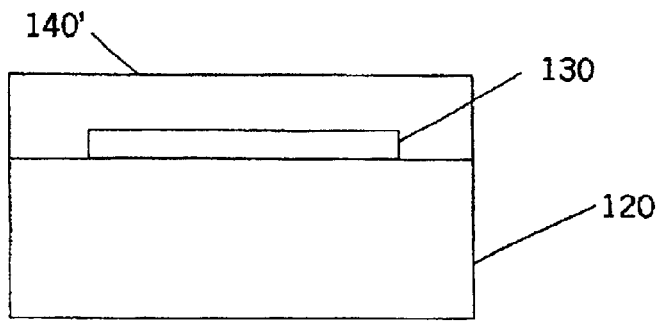

Referring now to FIG. 5F, a flexible dielectric layer 140', such as polyimide, is deposited, for example by spin coating, and is cured as desired. Then, referring to FIG. 5G, a conductive layer 150', such as gold, is blanket-deposited on the flexible dielectric layer 140'. As shown in FIG. 5H, the conductive layer 150' is patterned, for example using conventional photolithography, to form the patterned flexible upper electrode 150. The patterned flexible upper electrode 150 then is used as an etch mask to pattern the underlying dielectric layer 140', and thereby form the patterned flexible dielectric layer 140. A reactive ion etch or other dry etch may be used. Alternatively, a wet etch may be used. In other alternatives, the flexible dielectric layer 140' can be patterned in a first photolithography step and the conductive layer 150' can be patterned in a separate, second photolithography step. Appropriate bias voltages then may be applied, as was shown in FIG. 1, to establish horizontal and/or vertical current flow paths.

At least one coverlay sheet layer having an associated thickness also can be provided to overlie the substrate so as to sandwich the sensors or metallic pattern therebetween. The coverlay sheet can be a photosensitive and/or photoimageable coverlay dry film material. Examples of suitable coverlay materials include photoimageable polymers, acrylics, flexible composites, and derivatives thereof including, but not limited to, commercially available Pyralux® PC and Vacrel® from DuPont, and Conformask® from Morton. In addition, the coverlay sheet may be a pre-laminated sheet of a plurality of plies of one or more types and/or varying thickness of dry film coverlay materials and may also include desired coatings. The coverlay material maybe selected so as to be heat resistant or compatible with irradiation sterilization procedures as, in use, the sensor may be exposed to sterilization procedures, particularly for biomedical applications.

FIGS. 6A–6I are side cross-sectional views of chemical sensors according to other embodiments of the invention during intermediate fabrication steps according to embodiments of the invention. Embodiments of FIGS. 6A–6I may be used to form chemical sensors with patterned lower electrodes, such as illustrated in FIGS. 2–4.

Figure 6A:
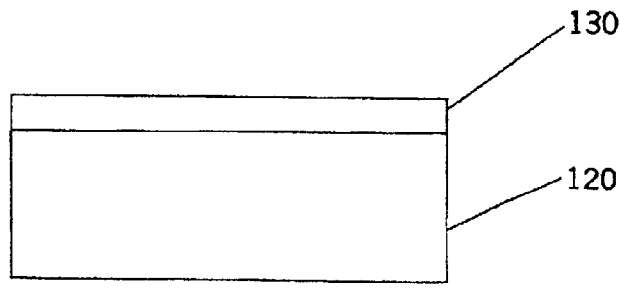
Figure 6B:
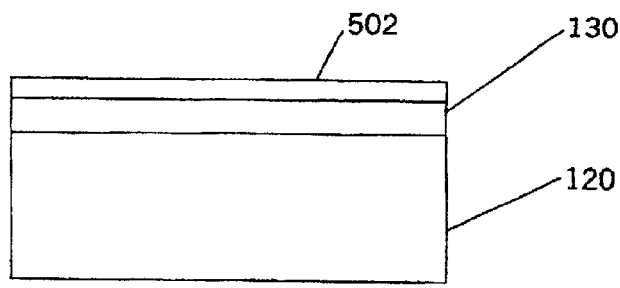

Referring now to FIGS. 6A and 6B, a photoresist 502 is formed or laminated on a flexible lower electrode 130, on a substrate 120, in a manner similar to that described for FIGS. 5A and 5B. Then, in FIG. 6C, a mask 604 is used to selectively expose the photoresist 502 to radiation 606. The resulting patterned photoresist 502" is developed in FIG. 6D, and the flexible lower electrode 130 then is etched using the patterned photoresist 502" in FIG. 6E, to thereby form the patterned flexible lower electrode 230.

Figure 5G:
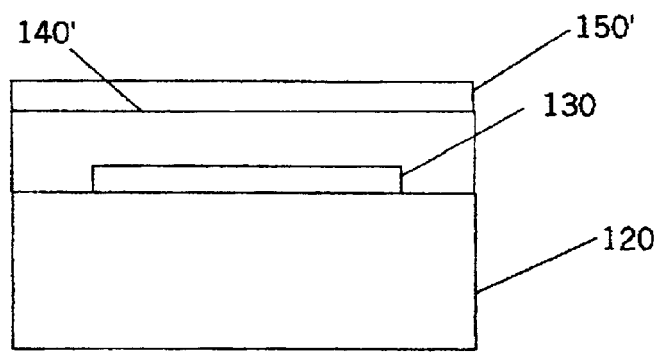
Figure 5H:
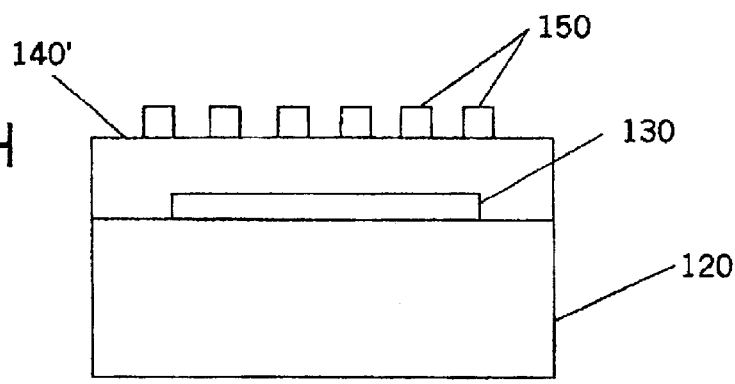
Figure 5I:
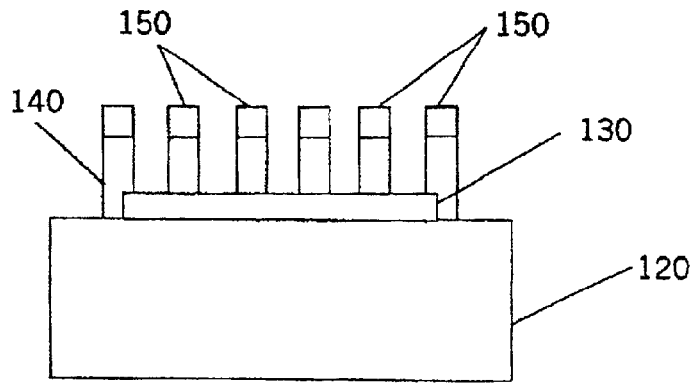
Figure 6C:
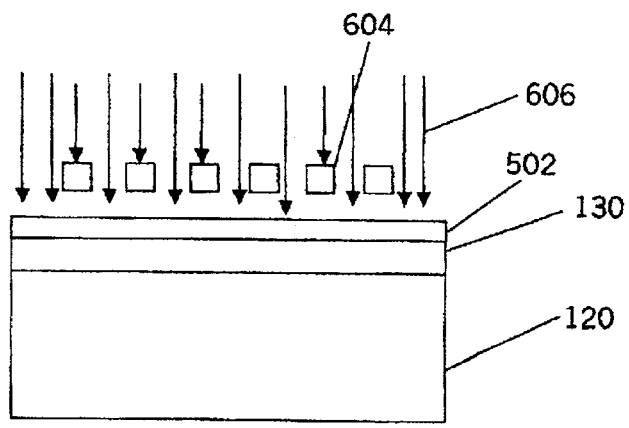
Figure 6D:
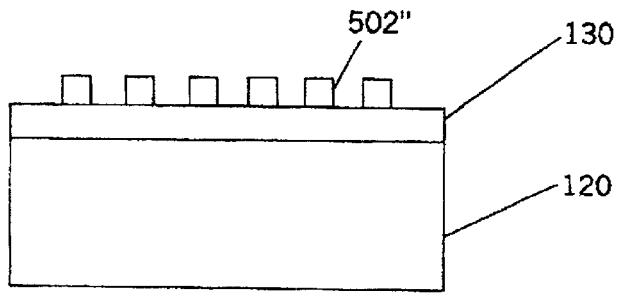
Figure 6E:
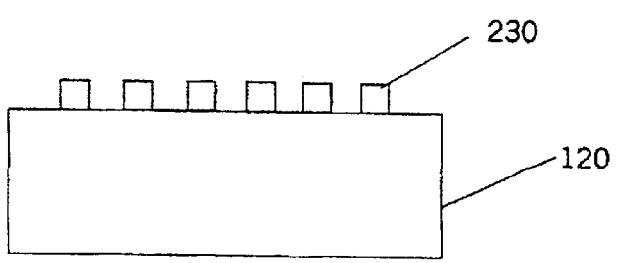
Figure 6F:
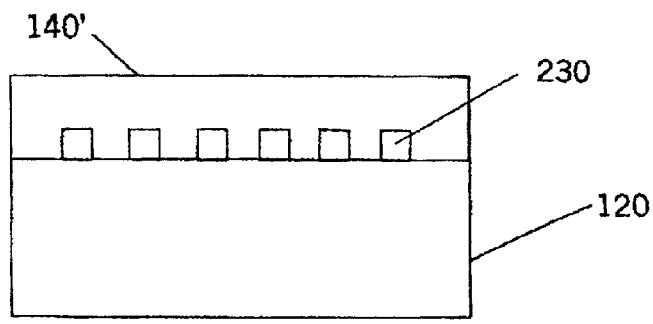
Figure 6G:
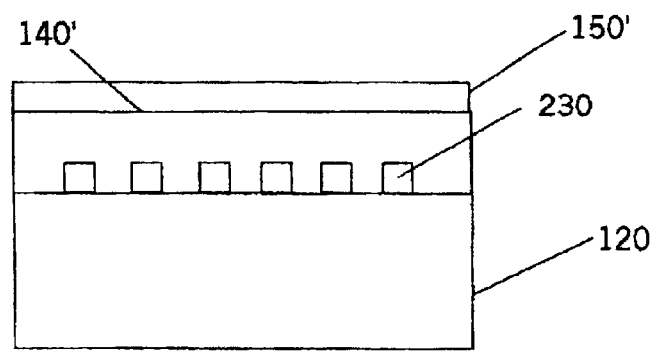
Figure 6H:
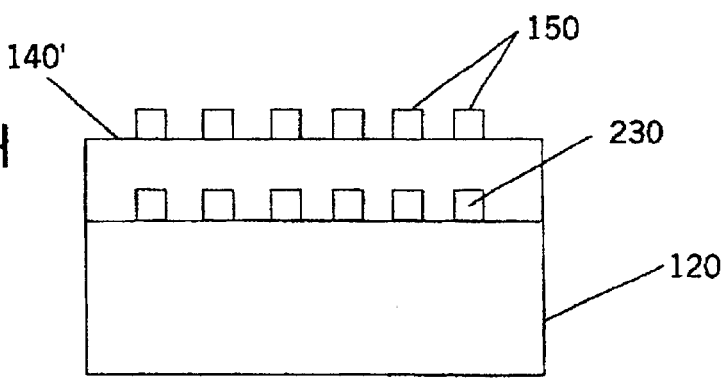

In FIGS. 6F–6H, the dielectric layer 140' and upper electrode layer 150' are formed and patterned, similar to that described in FIGS. 5F–5H. Finally, in FIG. 6I, the dielectric layer 140' is patterned using the patterned flexible upper electrode 150 as a mask, to thereby form the patterned flexible dielectric layer 140. A coverlay sheet layer also may be provided.

Figure 6I:
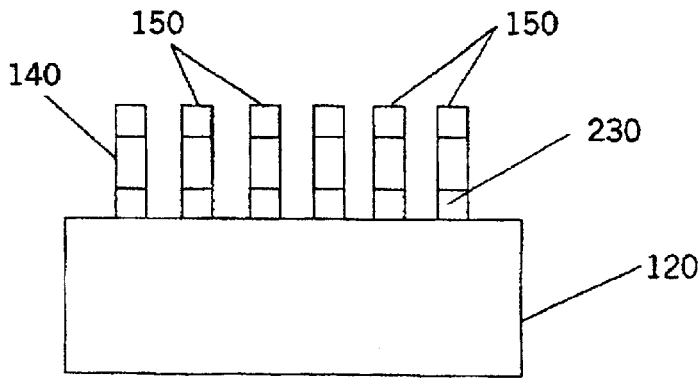

In method embodiments that were illustrated in FIGS. 6A–6I, the flexible lower electrode 230 is patterned at FIGS. 6C–6E, separate from the patterning of the flexible upper electrode 150 and the flexible dielectric layer 140 at FIGS. 6H and 6I. Separate patterning steps may be used according to these embodiments of the invention, to form separate contact structures that can supply the bias voltages that are shown in FIGS. 2–4, to the fingers of the upper and lower electrodes. However, in other embodiments, separate patterning of the lower electrode 230 need not be performed at FIGS. 6C–6E, and patterning of the lower electrode 230 may be accomplished by using the patterned flexible dielectric layer 140 as an etch mask for the lower electrode layer 130.

Figure 7:
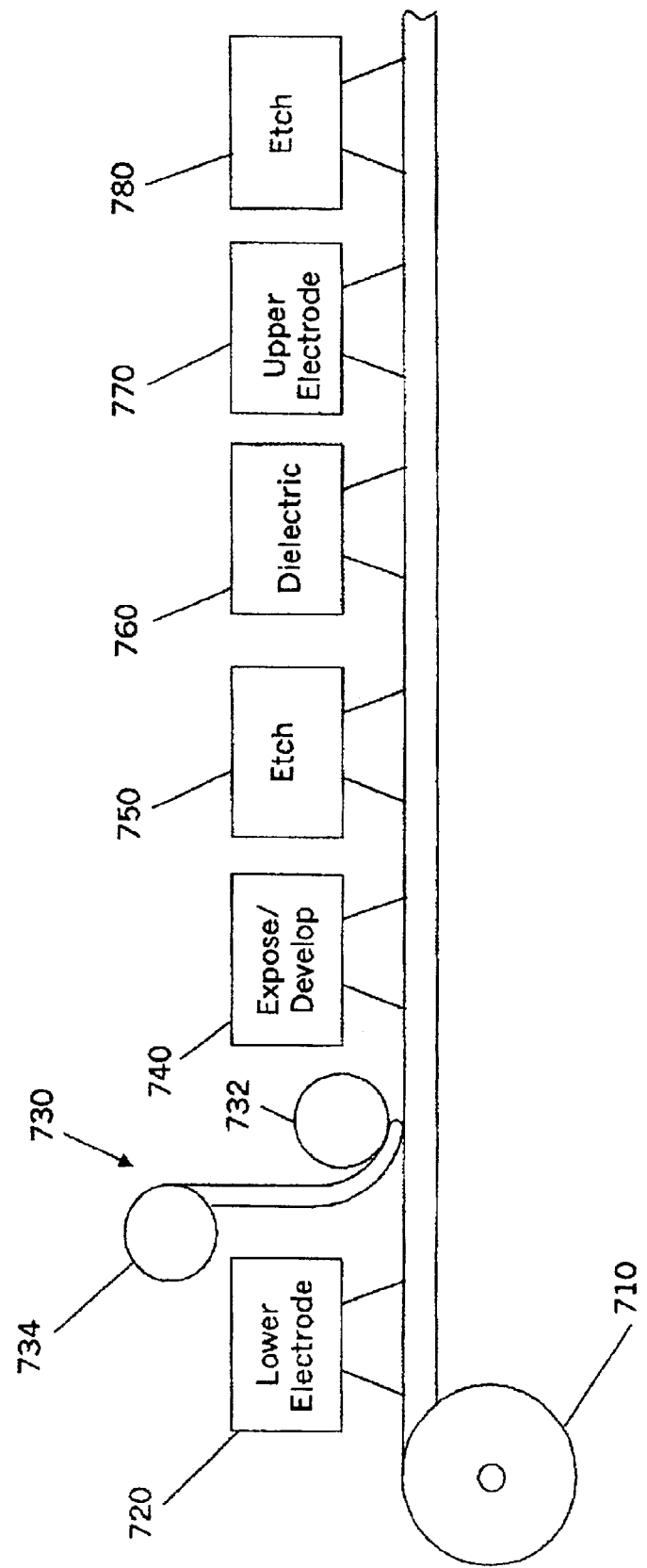
FIG. 7 is a schematic diagram of systems and methods for fabricating chemical sensors according to other embodiments of the present invention.

Referring now to FIG. 7, when flexible substrates are used, for example as was illustrated in FIGS. 1–3, 5A–5I and 6A–6I, continuous processing systems and methods may be used that are used in the fabrication of flexible ("flex") circuits. Thus, in embodiments of the invention, a continuous roll 710 of a flexible substrate 120, such as Kapton®, may be sequentially processed at a lower electrode station 720, a photoresist station 730, an expose/develop station 740, a first etch station 750, a dielectric station 760, an upper electrode station 770 and a second etch station 780, to fabricate chemical sensors according to these embodiments of the invention. The roll 710 of the flexible substrate 120 may be 24" wide by 2000' long. It will be understood that FIG. 7 conceptually illustrates the fabrication process, and any of the stations 720–780 may each include a plurality of substations. Moreover, operations of some of the stations 720–780 may be combined or eliminated.

The lower electrode station 720 can deposit a lower electrode 130, such as gold, on the flexible substrate 710, such as was described in connection with FIGS. 5A and 6A. Sputtering of gold and/or gold foil may be used. The photoresist station 730 can use a roller 732 to laminate photoresist from a roll of photoresist 734 on the substrate 710, as was described in connection with FIGS. 5B and 6B. The expose/develop station 740 may be used to expose and develop the photoresist, for example as was described in FIGS. 5C–5D and 6C–6D. A first etch station 750 may be used to etch the lower electrode 130/230 and strip the photoresist, as was described in connection FIGS. 5E and 6E. A dielectric station 760 may be used to laminate, spin coat and/or otherwise provide a dielectric layer 140' such as polyimide, as was described in FIGS. 5F and 6F. The polyimide may be cured. An upper electrode station 770 may be used to deposit, laminate and/or otherwise provide the upper electrode layer 150', as was described in connection with FIGS. 5G and 6G. The same operation of the lower electrode station 720 may be used. Finally, an etch station 780 may be used to perform the appropriate etching that was described in FIGS. 5H–5I and 6H–6I. Other stations may be used for pre- or post-processing steps. Thus, relatively low cost flexible circuit manufacturing techniques thus can be used to fabricate two-dimensional and/or three-dimensional current flow path chemical sensors.

It should be noted that, in some alternative embodiments of the present invention, the operations noted in FIGS. 5A–5I, 6A–6I and 7 may occur out of the order noted in the figures. For example, two operations shown in succession may in fact be performed substantially concurrently or the operations may sometimes be performed in the reverse order. In addition, other methods for forming one or more of the layers also may be employed.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A chemical sensor that senses a chemical, comprising:
   a flexible substrate;
   a flexible lower electrode on the flexible substrate;
   a patterned flexible dielectric layer on the flexible lower electrode opposite the flexible substrate; and
   a patterned flexible upper electrode on the patterned flexible dielectric layer opposite the flexible lower electrode, the patterned flexible dielectric layer and the patterned flexible upper electrode being patterned to provide at least one opening that exposes the flexible lower electrode to the chemical, if present, and to establish a current flow path between the flexible lower electrode and the patterned flexible upper electrode through the chemical, if present, upon application of voltage between the flexible lower electrode and the patterned flexible upper electrode.

2. A chemical sensor according to claim 1 wherein the flexible lower electrode and the patterned flexible upper electrode each comprises gold, platinum, palladium and/or copper.

3. A chemical sensor according to claim 1 wherein the substrate includes a substrate face, wherein the flexible lower electrode is on the substrate face and wherein the current flow path extends at least partially along a direction that is nonparallel to the substrate face.

4. A chemical sensor according to claim 1 wherein the substrate includes a substrate face, wherein the flexible lower electrode is on the substrate face and wherein the current flow path extends at least partially along a direction that is orthogonal to the substrate face.

5. A chemical sensor according to claim 1 wherein the flexible lower electrode is a patterned flexible lower electrode.

6. A chemical sensor that senses a chemical, comprising:
   a flexible substrate;
   a flexible lower electrode on the flexible substrate;
   a patterned flexible dielectric layer on the flexible lower electrode opposite the flexible substrate; and
   a patterned flexible upper electrode on the patterned flexible dielectric layer opposite the flexible lower electrode, the patterned flexible dielectric layer and the patterned flexible upper electrode being patterned to establish a current flow path between the flexible lower electrode and the patterned flexible upper electrode through the chemical, if present, upon application of voltage between the flexible lower electrode and the patterned flexible upper electrode;
   wherein the patterned flexible upper electrode includes a plurality of spaced apart fingers that are spaced apart from one another by at least an order of magnitude more than the thickness of the patterned flexible dielectric layer.

7. A chemical sensor according to claim 6 wherein the patterned flexible dielectric layer is between about one quarter micron and about two microns thick and wherein adjacent fingers in the plurality of spaced apart fingers are spaced apart from one another by about five microns to about fifty microns.

8. A chemical sensor that senses a chemical, comprising:
   a flexible substrate;
   a flexible lower electrode on the flexible substrate;
   a patterned flexible dielectric layer on the flexible lower electrode opposite the flexible substrate; and
   a patterned flexible upper electrode on the patterned flexible dielectric layer opposite the flexible lower electrode, the patterned flexible dielectric layer and the patterned flexible upper electrode being patterned to establish a current flow path between the flexible lower electrode and the patterned flexible upper electrode through the chemical, if present, upon application of voltage between the flexible lower electrode and the patterned flexible upper electrode;
   wherein the flexible lower electrode is an unpatterned flexible lower electrode.

9. A chemical sensor that senses a chemical, comprising:
   a flexible substrate;
   a flexible lower electrode on the flexible substrate;
   a patterned flexible dielectric layer on the flexible lower electrode opposite the flexible substrate; and
   a patterned flexible upper electrode on the patterned flexible dielectric layer opposite the flexible lower electrode, the patterned flexible dielectric layer and the patterned flexible upper electrode being patterned to establish a current flow path between the flexible lower electrode and the patterned flexible upper electrode through the chemical, if present, upon application of voltage between the flexible lower electrode and the patterned flexible upper electrode;
   wherein the flexible substrate comprises polyimide.

10. A chemical sensor that senses a chemical, comprising:
    a flexible substrate;
    a flexible lower electrode on the flexible substrate;
    a patterned flexible dielectric layer on the flexible lower electrode opposite the flexible substrate; and
    a patterned flexible upper electrode on the patterned flexible dielectric layer opposite the flexible lower electrode, the patterned flexible dielectric layer and the patterned flexible upper electrode being patterned to establish a current flow path between the flexible lower electrode and the patterned flexible upper electrode through the chemical, if present, upon application of voltage between the flexible lower electrode and the patterned flexible upper electrode;

wherein the flexible dielectric layer comprises polyimide, a Plasma Enhanced Chemical Vapor Deposition (PECVD) coating and/or a Diamond-Like Carbon (DLC) coating.

11. A chemical sensor that senses a chemical, comprising:

a flexible substrate;

a patterned flexible lower electrode on the flexible substrate;

a patterned flexible dielectric layer on the patterned flexible lower electrode opposite the flexible substrate; and a patterned flexible upper electrode on the patterned flexible dielectric layer opposite the patterned flexible lower electrode, the patterned flexible dielectric layer and the patterned flexible upper electrode being patterned to establish a current flow path between the patterned flexible lower electrode and the patterned flexible upper electrode through the chemical, if present, upon application of voltage between the patterned flexible lower electrode and the patterned flexible upper electrode;

wherein the patterned flexible lower electrode is patterned to establish a second current flow path between portions of the patterned flexible lower electrode through the chemical, if present, upon application of voltage between the portions of the patterned flexible lower electrode.

12. A chemical sensor according to claim 11 wherein the patterned flexible upper electrode is patterned to establish a third current flow path between portions of the patterned flexible upper electrode through the chemical, if present, upon application of voltage between the portions of the patterned flexible upper electrode.

13. A chemical sensor that senses a chemical, comprising:

a flexible substrate;

a flexible lower electrode on the flexible substrate;

a patterned flexible dielectric layer on the flexible lower electrode opposite the flexible substrate; and a patterned flexible upper electrode on the patterned flexible dielectric layer opposite the flexible lower electrode, the patterned flexible dielectric layer and the patterned flexible upper electrode being patterned to establish a current flow path between the flexible lower electrode and the patterned flexible upper electrode through the chemical, if present, upon application of voltage between the flexible lower electrode and the patterned flexible upper electrode;

wherein the patterned flexible upper electrode is patterned to establish a second current flow path between portions of the patterned flexible upper electrode through the chemical, if present, upon application of voltage between the portions of the patterned flexible upper electrode.

14. A chemical sensor that senses a chemical, comprising:

a flexible substrate;

a patterned flexible lower electrode on the flexible substrate;

a patterned flexible dielectric layer on the patterned flexible lower electrode opposite the flexible substrate; and a patterned flexible upper electrode on the patterned flexible dielectric layer opposite the patterned flexible lower electrode, the patterned flexible dielectric layer and the patterned flexible upper electrode being patterned to establish a current flow path between the patterned flexible lower electrode and the patterned flexible upper electrode through the chemical, if present, upon application of voltage between the patterned flexible lower electrode and the patterned flexible upper electrode;

wherein the patterned flexible upper electrode and the patterned flexible lower electrode both include a plurality of spaced apart fingers, the patterned flexible dielectric layer, the patterned flexible lower electrode and the patterned flexible upper electrode being patterned to establish a first current flow path between the patterned flexible lower electrode and the patterned flexible upper electrode through the chemical, if present, a second current flow path between adjacent fingers of the patterned flexible lower electrode through the chemical, if present, and a third current flow path between adjacent fingers of the patterned flexible upper electrode through the chemical, if present, upon application of voltage between the adjacent fingers of the patterned flexible lower electrode, between the adjacent fingers of the patterned flexible upper electrode and between adjacent fingers of the patterned upper and lower flexible electrodes.

15. A chemical sensor that senses a chemical, comprising:

a flexible substrate;

a patterned flexible lower electrode on the flexible substrate;

a patterned flexible dielectric layer on the patterned flexible lower electrode opposite the flexible substrate; and a patterned flexible upper electrode on the patterned flexible dielectric layer opposite the patterned flexible lower electrode, the patterned flexible dielectric layer and the patterned flexible upper electrode being patterned to establish a current flow path between the patterned flexible lower electrode and the patterned flexible upper electrode through the chemical, if present, upon application of voltage between the patterned flexible lower electrode and the patterned flexible upper electrode;

wherein the patterned flexible dielectric layer, the patterned flexible lower electrode and the patterned flexible upper electrode are patterned to establish a first current flow path between the patterned flexible lower electrode and the patterned flexible upper electrode through the chemical, if present, a second current flow path between portions of the patterned flexible lower electrode through the chemical, if present, and a third current flow path between portions of the patterned flexible upper electrode through the chemical, if present, upon application of voltage between the patterned flexible upper electrode and the patterned flexible lower electrode.

16. A chemical sensor that senses a chemical, comprising:

a substrate;

a lower electrode on the substrate;

a patterned dielectric layer on the lower electrode opposite the substrate; and a patterned upper electrode on the patterned dielectric layer opposite the lower electrode, the patterned dielectric layer and the patterned upper electrode being patterned to establish a first current flow path between the lower electrode and the patterned upper electrode through the chemical, if present, upon application of voltage between the lower electrode and the patterned upper electrode and to establish a second current flow path between portions of the patterned upper electrode through the chemical, if present, upon application of voltage between the portions of the patterned upper electrode.

17. A chemical sensor according to claim 16 wherein the substrate includes a substrate face, wherein the lower electrode is on the substrate face and wherein the first current flow path extends at least partially along a direction that is nonparallel to the substrate face.

18. A chemical sensor according to claim 16 wherein the substrate includes a substrate face, wherein the lower electrode is on the substrate face and wherein the first current flow path extends at least partially along a direction that is orthogonal to the substrate face.

19. A chemical sensor according to claim 16 wherein the lower electrode is a patterned lower electrode.

20. A chemical sensor according to claim 19 wherein the patterned lower electrode is patterned to establish a third current flow path between portions of the patterned lower electrode through the chemical, if present, upon application of voltage between the portions of the flexible lower electrode.

21. A chemical sensor that senses a chemical, comprising:
a substrate;
a lower electrode on the substrate;
a patterned dielectric layer on the lower electrode opposite the substrate; and
a patterned upper electrode on the patterned dielectric layer opposite the lower electrode, the patterned dielectric layer and the patterned upper electrode being patterned to establish a first current flow path between the lower electrode and the patterned upper electrode through the chemical, if present, upon application of voltage between the lower electrode and the patterned upper electrode and to establish a second current flow path between portions of the patterned upper electrode through the chemical, if present, upon application of voltage between the portions of the patterned upper electrode;
wherein the lower electrode is an unpatterned lower electrode.

22. A chemical sensor that senses a chemical, comprising:
a substrate;
a lower electrode on the substrate;
a patterned dielectric layer on the lower electrode opposite the substrate; and
a patterned upper electrode on the patterned dielectric layer opposite the lower electrode, the patterned dielectric layer and the patterned upper electrode being patterned to establish a first current flow path between the lower electrode and the patterned upper electrode through the chemical, if present, upon application of voltage between the lower electrode and the patterned upper electrode and to establish a second current flow path between portions of the patterned upper electrode through the chemical, if present, upon application of voltage between the portions of the patterned upper electrode;
wherein the patterned upper electrode includes a plurality of spaced apart fingers, the patterned dielectric layer and the patterned upper electrode being patterned to establish the first current flow path between the lower electrode and the patterned upper electrode through the chemical, if present, and the second current flow path between adjacent fingers of the patterned upper electrode through the chemical, if present, upon application of voltage between adjacent fingers of the patterned upper electrode and between the fingers of the patterned upper electrode and the lower electrode.

23. A chemical sensor that senses a chemical, comprising:
a substrate;
a patterned lower electrode on the substrate;
a patterned dielectric layer on the patterned lower electrode opposite the substrate; and
a patterned upper electrode on the patterned dielectric layer opposite the patterned lower electrode, the patterned dielectric layer and the patterned upper electrode being patterned to establish a first current flow path between the patterned lower electrode and the patterned upper electrode through the chemical, if present, upon application of voltage between the patterned lower electrode and the patterned upper electrode and to establish a second current flow path between portions of the patterned upper electrode through the chemical, if present, upon application of voltage between the portions of the patterned upper electrode;
wherein the patterned upper electrode and the patterned lower electrode both include a plurality of spaced apart fingers, the patterned dielectric layer, the patterned lower electrode and the patterned upper electrode being patterned to establish the first current flow path between the patterned lower electrode and the patterned upper electrode through the chemical, if present, the second current flow path between adjacent fingers of the patterned upper electrode through the chemical, if present, and a third current flow path between adjacent fingers of the patterned lower electrode through the chemical, if present, upon application of voltage between the adjacent fingers of the patterned lower electrode, between adjacent fingers of the patterned upper electrode and between adjacent fingers of the patterned upper and lower electrodes.

24. A chemical sensor that senses a chemical, comprising:
a substrate;
a lower electrode on the substrate;
an upper electrode on the lower electrode opposite the substrate and spaced apart from the lower electrode; and
means for establishing a first current flow path between the lower electrode and the upper electrode through the chemical, if present, upon application of voltage between the lower electrode and the upper electrode and for establishing a second current flow path between portions of the upper electrode through the chemical, if present, upon application of voltage between the portions of the upper electrode.

25. A chemical sensor according to claim 24 wherein the substrate includes a substrate face, wherein the lower electrode is on the substrate face and wherein the first current flow path extends at least partially along a direction that is nonparallel to the substrate face.

26. A chemical sensor according to claim 24 wherein the substrate includes a substrate face, wherein the lower electrode is on the substrate face and wherein the first current flow path extends at least partially along a direction that is orthogonal to the substrate face.

27. A chemical sensor according to claim 24 wherein the means for establishing further comprises means for establishing a third current flow path between portions of the lower electrode through the chemical, if present, upon application of voltage between the portions of the lower electrode.

28. A method of fabricating a chemical sensor that senses a chemical, comprising:

forming a flexible lower electrode on a flexible substrate;

forming a flexible dielectric layer on the flexible lower electrode opposite the flexible substrate;

forming a patterned flexible upper electrode on the flexible dielectric layer opposite the flexible lower electrode; and patterning the flexible dielectric layer using the patterned flexible upper electrode as a mask to establish a current flow path between the flexible lower electrode and the patterned flexible upper electrode through the chemical, if present, upon application of voltage between the flexible lower electrode and the patterned flexible upper electrode.

29. A method according to claim 28 wherein the forming a patterned flexible upper electrode comprises forming a patterned flexible upper electrode that includes a plurality of spaced apart fingers that are spaced apart from one another by at least an order of magnitude more than the thickness of the flexible dielectric layer.

30. A method according to claim 28 wherein the flexible substrate comprises polyimide.

31. A method according to claim 28 wherein the flexible dielectric layer comprises polyimide, a Plasma Enhanced Chemical Vapor Deposition (PECVD) coating and/or a Diamond-Like Carbon (DLC) coating.

32. A method according to claim 28 wherein the flexible lower electrode and the patterned flexible upper electrode each comprises gold, platinum, palladium and/or copper.

33. A method according to claim 28 wherein the forming a flexible lower electrode comprises forming a patterned flexible lower electrode on a flexible substrate.

34. A method according to claim 28 wherein the following is performed between the forming a flexible lower electrode and the forming a flexible dielectric layer:

laminating a flexible photoresist layer onto the flexible lower electrode;

selectively exposing and developing the flexible photoresist layer; and patterning the flexible lower electrode using the flexible photoresist layer that has been exposed and developed as a mask; and removing the flexible photoresist layer that has been exposed and developed from the flexible lower electrode layer that has been patterned.

35. A method according to claim 28 wherein the forming a patterned flexible upper electrode comprises:

forming a flexible upper electrode layer on the flexible dielectric layer;

laminating a flexible photoresist layer onto the flexible upper electrode layer;

selectively exposing and developing the flexible photoresist layer; and patterning the flexible upper electrode layer using the flexible photoresist layer that has been exposed and developed as a mask; and removing the flexible photoresist layer that has been exposed and developed from the flexible upper electrode layer that has been patterned.

36. A method according to claim 28 wherein the patterning the flexible dielectric layer comprises reactive ion etching the flexible dielectric layer using the patterned flexible upper electrode as a mask.

37. A method of fabricating a plurality of chemical sensors that sense a chemical, comprising:

forming a series of laterally spaced apart flexible lower electrodes on a flexible substrate;

forming a flexible dielectric layer on the series of laterally spaced apart flexible lower electrodes opposite the flexible substrate;

forming a series of patterned flexible upper electrodes on the dielectric layer, a respective one of which is opposite a respective one of the series of flexible lower electrodes; and patterning the flexible dielectric layer using the series of patterned flexible upper electrodes as a mask to establish a current flow path between a respective flexible lower electrode and a respective patterned flexible upper electrode through the chemical, if present, upon application of voltage between the flexible lower electrode and the patterned flexible upper electrode.

38. A method according to claim 37 wherein the forming a series of patterned flexible upper electrodes comprises forming a series of patterned flexible upper electrodes that each includes a plurality of spaced apart fingers that are spaced apart from one another by at least an order of magnitude more than the thickness of the flexible dielectric layer.

39. A method according to claim 37 wherein the flexible substrate comprises polyimide.

40. A method according to claim 37 wherein the flexible dielectric layer comprises polyimide, a Plasma Enhanced Chemical Vapor Deposition (PECVD) coating and/or a Diamond-Like Carbon (DLC) coating.

41. A method according to claim 37 wherein the flexible lower electrode and the patterned flexible upper electrode each comprises gold, platinum, palladium and/or copper.

42. A method according to claim 37 wherein the forming a series of laterally spaced apart flexible lower electrodes comprises:

forming a flexible lower electrode layer on the flexible substrate;

laminating a flexible photoresist layer onto the flexible lower electrode layer;

selectively exposing and developing the flexible photoresist layer;

patterning the flexible lower electrode layer using the flexible photoresist layer that has been exposed and developed as a mask; and removing the flexible photoresist layer that has been exposed and developed from the flexible lower electrode layer that has been patterned.

43. A method according to claim 37 wherein the forming a series of patterned flexible upper electrodes on the dielectric layer comprises:

forming a flexible upper electrode layer on the flexible dielectric layer;

laminating a flexible photoresist layer onto the flexible upper electrode layer;

selectively exposing and developing the flexible photoresist layer;

patterning the flexible upper electrode layer using the flexible photoresist layer that has been exposed and developed as a mask; and removing the flexible photoresist layer that has been exposed and developed from the flexible upper electrode layer that has been patterned.

44. A method according to claim 37 wherein the patterning the flexible dielectric layer comprises reactive ion etching the flexible dielectric layer using the series of patterned flexible upper electrodes as a mask.

45. A method of sensing a chemical using a chemical sensor that includes a substrate, a patterned lower electrode on the substrate, a patterned dielectric layer on the lower electrode opposite the substrate and a patterned upper electrode on the patterned dielectric layer opposite the lower electrode, the method comprising:

applying voltage between adjacent portions of the patterned upper electrode, between adjacent portions of the patterned lower electrode and between adjacent portions of the patterned upper and lower electrodes, while the chemical sensor is potentially exposed to the chemical.

46. A method according to claim 45 wherein the patterned upper electrode and the patterned lower electrode both include a plurality of spaced apart fingers, and wherein the applying comprises:

applying voltage between adjacent spaced apart fingers of the patterned upper electrode, between adjacent spaced apart fingers of the patterned lower electrode and between adjacent fingers of the patterned upper and lower electrodes, while the chemical sensor is potentially exposed to the chemical.

* * * * *